US012746175B2

(12) United States Patent
Jeong et al.

(10) Patent No.: US 12,746,175 B2
(45) Date of Patent: Sep. 29, 2026

(54) MASSAGE APPARATUS

(71) Applicant: Samsung Electronics Co., Ltd., Suwon-si (KR)

(72) Inventors: Jiho Jeong, Suwon-si (KR); Daesung Ki, Suwon-si (KR); Sunggyun Park, Suwon-si (KR); Semin Lee, Suwon-si (KR); Kunwoo Baek, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 731 days.

(21) Appl. No.: 18/141,353

(22) Filed: Apr. 28, 2023

(65) Prior Publication Data

US 2024/0033168 A1 Feb. 1, 2024

Related U.S. Application Data

(63) Continuation of application No. PCT/KR2023/005280, filed on Apr. 19, 2023.

(30) Foreign Application Priority Data

Jul. 28, 2022 (KR) .................. KR10-2022-0094252

(51) Int. Cl.

*A61H 15/02* (2006.01)
*A61F 7/00* (2006.01)
*A61H 15/00* (2006.01)

(52) U.S. Cl.

CPC ......... *A61H 15/02* (2013.01); *A61H 15/0078* (2013.01); *A61F 2007/0093* (2013.01); (Continued)

(58) Field of Classification Search

CPC .............. A61H 7/00; A61H 2201/0149; A61H 1/001–005; A61H 1/0237–0266; A61H 1/0285

See application file for complete search history.

(56) References Cited

U.S. PATENT DOCUMENTS

| | | | | |
|---|---|---|---|---|
| 6,190,339 B1 | 2/2001 | Imazaike et al. | | |
| 11,103,673 B2 | 8/2021 | Bae et al. | | |
| 2002/0177796 A1* | 11/2002 | Suh | ........................ | A61H 7/001 601/84 |

(Continued)

FOREIGN PATENT DOCUMENTS

| | | |
|---|---|---|
| CN | 212997362 U | 4/2021 |
| JP | 4638760 B2 | 2/2011 |

(Continued)

OTHER PUBLICATIONS

Machine translation of KR-20130002405-U. Access from PE2E search tool on Jan. 2026. (Year: 2013).*

International Search Report for International Application No. PCT/KR2023/005280; International Filing Date Apr. 19, 2023; Date of Mailing Aug. 7, 2023; 7 Pages.

*Primary Examiner* — Joseph D. Boecker
*Assistant Examiner* — Jaeick Jang
(74) *Attorney, Agent, or Firm* — CANTOR COLBURN LLP

(57) ABSTRACT

Provided is a massage apparatus including a base frame, a seat frame coupled to the base frame to form a seating surface on one side, a massage module disposed between the base frame and the seat frame and provided to be movable along the seating surface on a rear side of the seating surface, and an auxiliary massage module formed to pass through the seat frame. The auxiliary massage module may include a rotating member connected to a module mounting portion of the base frame that forms a rotation axis of the auxiliary massage module, a support member formed to extend forward from the rotating member and having a shoulder massage case, and an extension member formed to extend downward from the support member and having an abdominal massage case.

16 Claims, 7 Drawing Sheets

(52) U.S. Cl.
CPC ................ *A61H 2201/0107* (2013.01); *A61H 2201/0149* (2013.01); *A61H 2201/0207* (2013.01); *A61H 2201/1614* (2013.01); *A61H 2201/5007* (2013.01); *A61H 2203/0431* (2013.01); *A61H 2205/062* (2013.01); *A61H 2205/083* (2013.01)

(56) References Cited

U.S. PATENT DOCUMENTS

| | | | | |
|---|---|---|---|---|
| 2019/0231634 | A1 | 8/2019 | Inada | |
| 2020/0397644 | A1* | 12/2020 | Jung | A47C 7/62 |
| 2022/0256992 | A1* | 8/2022 | Williams | A61H 33/6089 |

FOREIGN PATENT DOCUMENTS

| | | | | |
|---|---|---|---|---|
| JP | 2011067452 A | 4/2011 | | |
| JP | 4773272 B2 | 9/2011 | | |
| KR | 20020089883 A | 11/2002 | | |
| KR | 20070105590 A | 10/2007 | | |
| KR | 20130002405 A | 1/2013 | | |
| KR | 20130002405 U | * | 4/2013 | A61H 7/007 |
| KR | 20170127777 A | 11/2017 | | |
| KR | 101883306 B1 | 7/2018 | | |
| KR | 20190001023 U | 4/2019 | | |
| KR | 101953583 B1 | 5/2019 | | |
| KR | 20190093142 A | 8/2019 | | |
| KR | 20220042006 A | 4/2022 | | |

* cited by examiner

MASSAGE APPARATUS

CROSS-REFERENCE TO RELATED APPLICATIONS

This application is a continuation application, claiming priority under § 365(c), of International Application No. PCT/KR2023/005280, filed on Apr. 19, 2023, which is based on and claims the benefit of Korean patent application number filed on Jul. 28, 2022, in the Korean Intellectual Property Office, the disclosures of which are incorporated by reference herein in their entireties.

TECHNICAL FIELD

The present disclosure relates to an improved structure of a massage apparatus.

BACKGROUND ART

A massage apparatus is an apparatus that allows a user to receive a massage while being seated, and provides a massage over all areas of the user's body.

Typically, massage apparatuses may be provided as a chair-type structure massage apparatus or a bed-type structure massage apparatus.

In this case, while massage on a rear surface of the user's body can be performed, it may be difficult to perform massage on a front surface of the user's body.

One aspect of the disclosure provides a massage apparatus having an improved structure to massage a front surface of a user's body.

SUMMARY

A massage apparatus according to an aspect of the disclosure includes a base frame. The massage apparatus includes a seat frame coupled to the base frame to form a seating surface on one side. The massage apparatus includes a massage module disposed between the base frame and the seat frame and provided to be movable along the seating surface on a rear side of the seating surface. The massage apparatus includes an auxiliary massage module formed to pass through the seat frame. The auxiliary massage module of the massage apparatus includes a rotating member connected to a module mounting portion of the base frame that forms a rotation axis of the auxiliary massage module. The auxiliary massage module of the massage apparatus includes a support member formed to extend forward from the rotating member and having a shoulder massage case. The auxiliary massage module of the massage apparatus includes an extension member formed to extend downward from the support member and having an abdominal massage case.

The massage apparatus may further include a shoulder massage ball accommodated in the shoulder massage cases and protruding toward the seating surface.

The massage apparatus may further include a heating element accommodated in the abdominal massage case.

The massage apparatus may further include an abdominal massage ball accommodated in the abdominal massage case and protruding from the extension member toward the seating surface.

The extension member may be provided in a pair, and the abdominal massage cases may be respectively connected to the pair of extension members to cover an abdomen of a user seated on the seating surface.

The abdominal massage case may be provided therein with an accommodation space, and the heating element may be accommodated in the accommodation space.

The support member may be integrally formed with the extension member.

The support member may include a support bar connecting the rotating member to the shoulder massage case.

The support bar may extend in a direction away from the seating surface to be located on an upper side of a shoulder of a user seated on the seating surface.

The extension member may include a connecting bar that includes a bent portion connecting the shoulder massage case to the abdominal massage case and formed to bend and extend downward from the shoulder massage case.

The connecting bar may include a guard portion connecting the bent portion to the abdominal massage case and positioned on a front of a user seated on the seating surface.

The seat frame may include a module passing portion formed as an opening in a portion of the seating surface to be positioned on a front of the module mounting portion so that the auxiliary massage module may pass therethrough.

The massage apparatus may further include: a controller configured to control operations of the massage module and the auxiliary massage module; and a rotational driver configured to provide rotational power for rotating the auxiliary massage module, and the controller may control the rotational driver to move the auxiliary massage module toward the seating surface so that a user may be kept seated on the seating surface.

The massage apparatus may further include: an abdominal massage ball accommodated inside the abdominal massage case; and a massage ball driver configured to drive the abdominal massage ball, and the controller may control the massage ball driver to perform an abdominal massage mode.

The massage apparatus may further include a heating element accommodated inside the abdominal massage cases, and the controller may control a heating temperature of the heating element to perform an abdominal heating mode.

A portion of the shoulder massage case may include an elastically deformable material, and wherein a shoulder massage ball is configured to acupressure a shoulder of a user inside of the shoulder massage case using the elastically deformable.

An auxiliary massage module coupled to a front side of a massage apparatus is provided, and thus massage on a front surface of the user's body can be performed with a simple operation.

A close contact between a user and a massage apparatus is assisted through an auxiliary massage module, and thus the massage efficiency of the massage apparatus can be increased.

Massaging of the user's abdomen can be performed using an auxiliary massage module.

MODES OF THE DISCLOSURE

Figure 1:
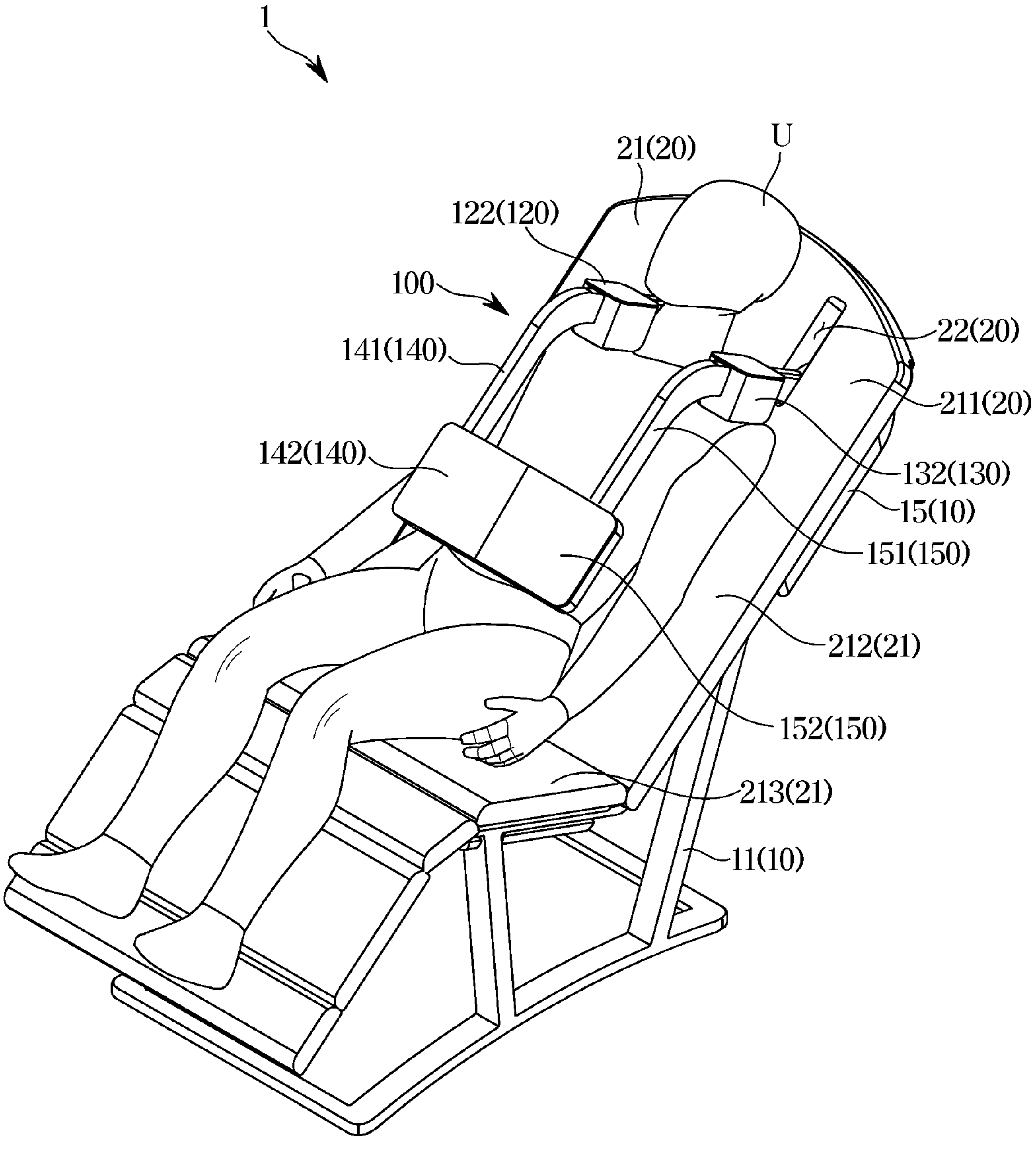
FIG. 1 is a perspective view illustrating a massage apparatus according to an embodiment of the disclosed disclosure.

Embodiments described in the specification and configurations shown in the accompanying drawings are merely exemplary examples of the present disclosure, and various modifications may replace the embodiments and the drawings of the present disclosure at the time of filing of the present application.

Further, identical symbols or numbers in the drawings of the present disclosure denote components or elements configured to perform substantially identical functions.

Further, terms used herein are only for the purpose of describing particular embodiments and are not intended to limit to the present disclosure. The singular form is intended to include the plural form as well, unless the context clearly indicates otherwise. It should be further understood that the terms “include,” “including,” “have,” and/or “having” specify the presence of stated features, integers, steps, operations, elements, components, and/or groups thereof, but do not preclude the presence or addition of one or more other features, integers, steps, operations, elements, components, and/or groups thereof.

Further, it should be understood that, although the terms “first,” “second,” etc., may be used herein to describe various elements, the elements are not limited by the terms, and the terms are only used to distinguish one element from another. For example, a first element could be termed a second element, and similarly, a second element could be termed a first element without departing from the scope of the present disclosure. The term “and/or” includes combinations of one or all of a plurality of associated listed items.

Hereinafter, embodiments according to the disclosure will be described in detail with reference to the accompanying drawings.

FIG. 1 is a perspective view illustrating a massage apparatus according to an embodiment of the disclosed disclosure.

A massage apparatus 1 is an apparatus that provides a user (U) with a massage. The massage apparatus 1 may be implemented in the form of a chair in which a user may take a rest while being seated or lying down.

The massage apparatus 1 may include a base frame 10 and a seat frame 20.

The seat frame 20 may be coupled to the base frame 10 to form a seating surface 21 on one side. For example, the seat frame 20 may be coupled to the front of the base frame 10 such that a user’s body is seated and supported thereon.

The seat frame 20 may be formed to extend longitudinally to support body parts of the user U from the head to the upper body, buttocks and lower body. In addition, the seat frame 20 is not limited to the shape shown in FIG. 1 and may be formed to surround each body part of the user.

The seating surface 21 of the seat frame 20 may be provided to be in contact with the body of the user. For example, the seating surface 21 of the seat frame 20 may be in contact with the rear surface of the user to support the user on the rear side of the user.

The seating surface 21 of the seat frame 20 may include a soft material to enhance the seating comfort of the user. For example, the seating surface 21 of the seat frame 20 may include leather or cloth material. Accordingly, the seating surface 21 may provide psychological stability to the user.

In addition, the seating surface 21 of the seat frame 20 may include a deformable material for the rear surface of the body of the user to be pressed by a massage module (D in FIG. 5) on the rear side of the seat frame 20. However, the material forming the seating surface 21 is not limited thereto and may be variously provided as long as it can provide comfort to the user.

The seating surface 21 may include a first seating portion 211, a second seating portion 212, and a third seating portion 213.

In the following description, the upper body and the lower body of the user may be distinguished based on the buttocks of the user.

The first seating portion 211 may be provided to support a part or entirety of the user’s head among the body parts of the user.

The second seating portion 212 may be connected to the first seating portion 211 and may be positioned on a lower side of the first seating portion 211. The second seating portion 212 may be provided to support a part or entirety of the user’s upper body among the body parts of the user. In addition, the second seating portion 212 may be provided to support a rear part of the user’s buttocks among lower body parts of the user.

The third seating portion 213 may be connected to the second seating portion 212 and may be positioned on a lower side of the second seating portion 212. The third seating portion 213 may be provided to support a part or entirety of the user’s lower body among the body parts of the user.

For example, the first seating portion 211 and the second seating portion 212 may support a part or entirety of the upper body including the user’s head on the rear side of the user. The third seating portion 213 may support a part or entirety of the user’s lower body on the rear side of the user.

The first seating portion 211 and the second seating portion 212 may be integrally formed with each other. However, it is not limited thereto, and the first seating portion 211 and the second seating portion 212 may be provided in separate parts. For example, the first seating portion 211 may be movably provided with respect to the second seating portion 212 such that an angle at which the first seating portion 211 supports the user’s head is adjusted.

However, it is not limited thereto, and the first seating portion 211 may be connected to the second seating portion 212 to be fixed to the second seating portion 212.

The second seating portion 212 may be movably provided with respect to the third seating portion 213 such that the angle at which the second seating portion 212 supports the user’s upper body is adjusted. For example, the second seating portion 212 may be provided to pivot forward and backward with respect to the third seating portion 213 based on a point at which the second seating portion 212 is connected to the third seating portion 213.

However, it is not limited thereto, and the second seating portion 212 may be connected to the third seating portion 213 to be fixed to the third seating portion 213.

The third seating portion 213 may be provided to support the user’ thighs and calves on the rear side of the user. The third seating portion 213 may be divided into a portion supporting the user’s thighs and a portion supporting the user’s calves.

The portion supporting the user's thighs in the third seating portion 213 may be formed to be inclined backward.

The portion supporting the calves of the user in the third seating portion 213 is provided to be pivoted with respect to the portion supporting the thighs of the user such that the angle of supporting the calves of the user may be adjusted.

In addition, although not shown in the drawings, the portion supporting the calves of the user in the third seating portion 213 may be provided in a shape surrounding the calves of the user such that the calves of the user may be accommodated therein.

The base frame 10 may include a support body 12, a support leg 11, and a rear cover 15.

The support body 12 may be coupled to the rear side of the seat frame 20 to support the rear surface of the seat frame 20. The support body 12 may be coupled to the seat frame 20 to support a portion of the edge of the seat frame 20.

The rear cover 15 may be disposed on the rear side of the support body 12 to form a part of the rear exterior of the massage apparatus 1. The massage module (D in FIG. 5) may be disposed between the rear cover 15 and the seat frame 20.

The support leg 11 may extend downward from the support body 12 and may be supported on an installation surface. The installation surface may refer to a surface forming the floor of a place in which the massage apparatus 1 is placed.

The support body 12 may be coupled to be rotatable with respect to the support leg 11. Therefore, the support body 12 may be adjusted in angle together with the seat frame 20. Details of the seat frame 20 and base frame 10 of the massage device 1 according to an embodiment of the disclosure will be described below.

The seat frame 20 and the base frame 10 shown in FIG. 1 are merely one example of the disclosure, and the seat frame 20 and the base frame 10 may be provided in various shapes that support the body of the user.

Although not shown in the drawing, the seat frame 20 may include an armrest for supporting the arms of the user.

Although not shown in the drawings, a housing covering the base frame 10 may be provided on the outside of the base frame 10. In addition, the housing may be provided to cover the outside of the seat frame 20. The housing may be provided to cover the upper, lower, left, and right sides of the user in a state in which the user is seated on the seat frame 20.

However, it is not limited thereto, and the housing may be provided in various shapes to form the appearance of the massage apparatus 1 while improving the overall aesthetics.

In addition, the housing may be provided to cover at least a portion of the upper, lower, left, and right sides of the user such that the user using the massage apparatus 1 feels isolated from the external environment.

In addition, a manipulator (M in FIG. 7) for inputting a command of the user may be formed on one surface of the housing. The user may input a command to the massage apparatus 1 through the manipulator M, and the command input through the manipulator M may be received by a controller C of the massage apparatus 1 such that various massage modes are performed.

However, the input method of the manipulator M is not limited thereto, and the command of the user may be received by the controller C through remote control of a wireless communication method. For example, the controller C may include a wireless transceiver that is configured to communicate with a smartphone of a user.

The seat frame 20 may include a module passing portion 22.

The module passing portion 22 may be provided for an auxiliary massage module 100 to pass through the seat frame 20. The module passing portion 22 may be formed as an opening in a portion of the seating surface 21 of the seat frame 20. The module passing portion 22 may be formed on a front side of a module mounting portion (14 in FIG. 2) to be described below.

The module passing portions 22 may be respectively formed on both sides of the user's head, on the seating surface 21 of the seat frame 20. For example, the module passing portions 22 may be formed in a pair on both sides of the user's head.

The massage apparatus 1 may include the auxiliary massage module 100.

The auxiliary massage module 100 may be provided to pass through the seat frame 20 and rotate on the front side of the seating surface 21. The auxiliary massage module 100 may be disposed on the front side of the user's body.

For example, the auxiliary massage module 100 may be provided to press the front surface of the user's body. In addition, the auxiliary massage module 100 may be provided to press the user's shoulder. Details thereof will be described below.

Figure 2:
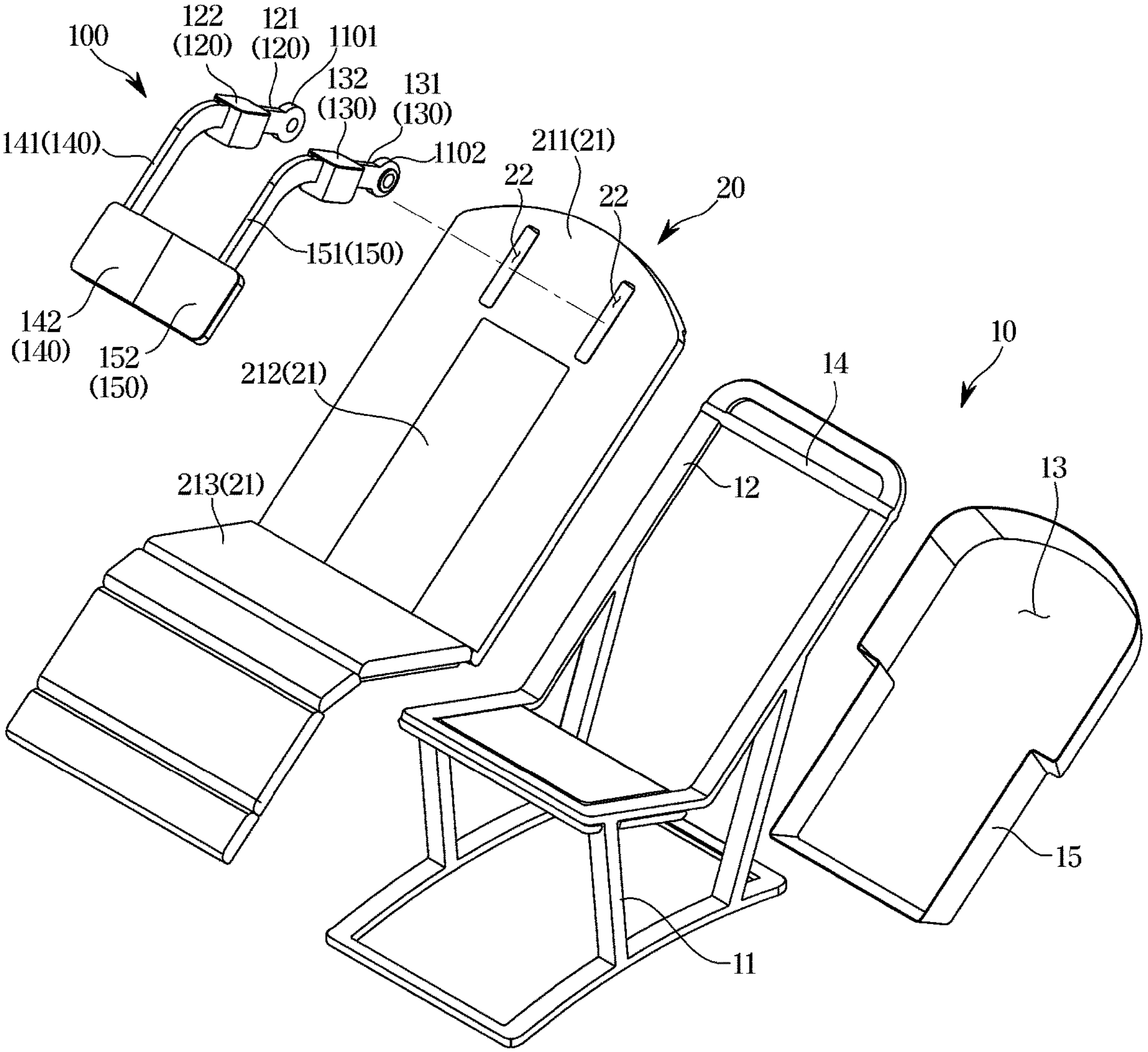
FIG. 2 is a disassembled perspective view illustrating the massage apparatus shown in FIG. 1.
Figure 3:
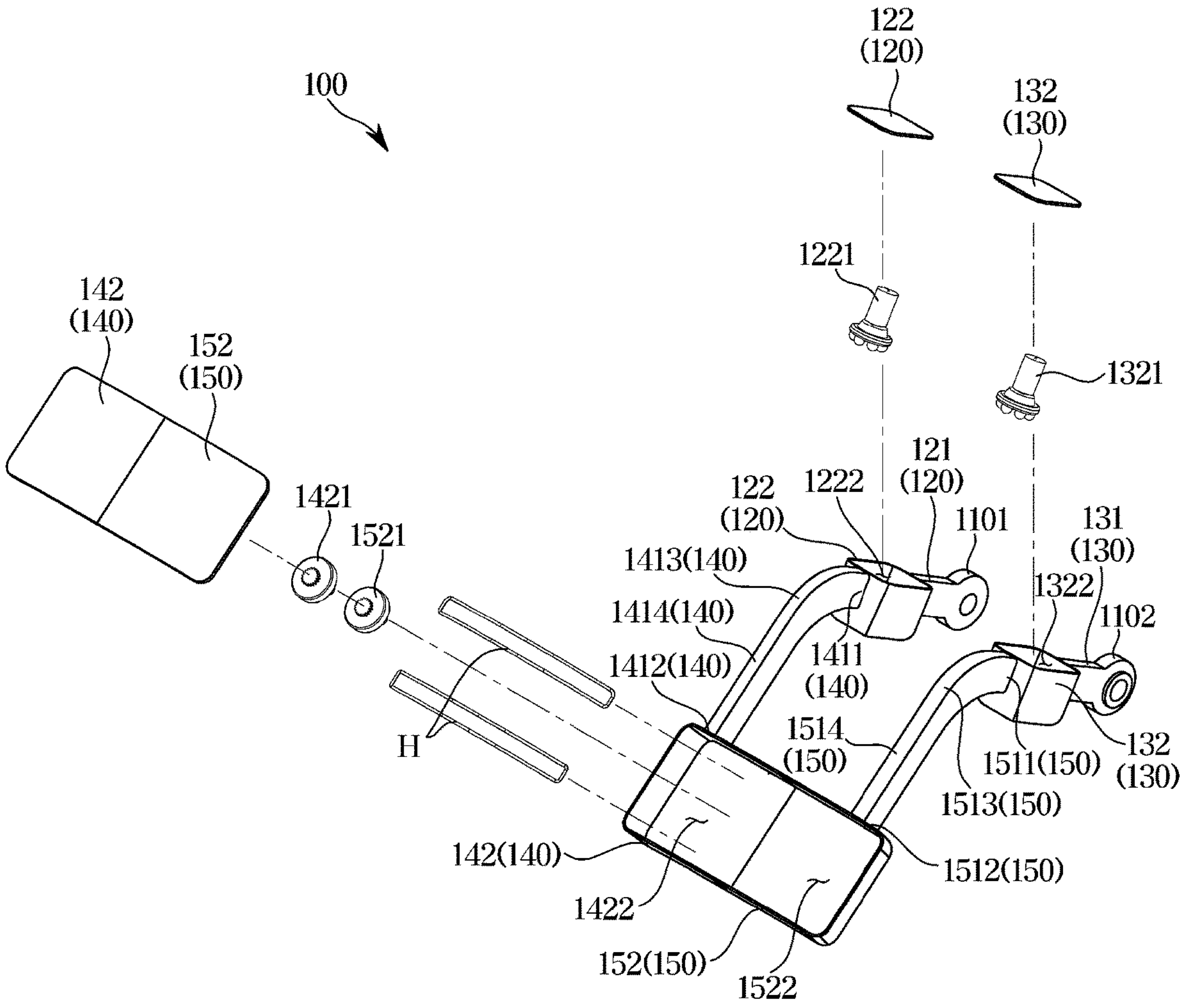
FIG. 3 is a disassembled perspective view illustrating an auxiliary massage module shown in FIG. 2.

FIG. 2 is a disassembled perspective view illustrating the massage apparatus shown in FIG. 1. FIG. 3 is a disassembled perspective view illustrating the auxiliary massage module shown in FIG. 2.

Referring to FIGS. 1 and 2, the massage apparatus 1 may include a seat frame 20 forming the seating surface 21 and a base frame 10 coupled to the rear side of the seat frame 20.

The massage apparatus 1 may include an auxiliary massage module 100 that is formed to protrude forward of the seat frame 20.

The auxiliary massage module 100 may be formed to extend from the rear of the seat frame 20 to the front of the seat frame 20 and move toward or away from the seating surface 21 of the seat frame 20.

The base frame 10 may include a support body 12 and a support leg 11. As described above, the support leg 11 may be provided to support the massage apparatus 1 while in contact with the installation surface of the massage apparatus 1. The support leg 11 may extend downward from the support body 12.

The support body 12 may be coupled to the rear side of the seat frame 20 to support the rear surface of the seat frame 20.

The base frame 10 may include a rear cover 15. The rear cover 15 may be coupled to the rear side of the support body 12 and the support leg 11 to form a part of the rear surface of the base frame 10.

The rear cover 15 may be provided as a housing with one surface open. The rear cover 15 may form an accommodation space 13 therein. Driving devices, such as a massage module D, may be accommodated and/or disposed in the accommodation space 13 formed inside the rear cover 15.

For example, the base frame 10 may be disposed between the seat frame 20 and the rear cover 15, and the massage module D, a module driving device for driving the massage module D, and the like may be disposed between the seat frame 20 and the rear cover 15.

The base frame 10 may include a module mounting portion 14. The module mounting portion 14 may form a rotation axis of the auxiliary massage module 100. The module mounting portion 14 may extend along the left and right directions of the base frame 10. The auxiliary massage module 100 may be rotatably coupled to the module mounting portion 14.

The module mounting portion 14 may have a cross section in a circular shape. The module mounting portion 14 may be provided in a bar shape extending along the left and right directions of the massage apparatus 1. However, the shape of the module mounting portion 14 is not limited thereto, and the module mounting portion 14 may be provided in various shapes that are configured to support a rotating member of the auxiliary massage module 100 to be described below.

In addition, the position of the module mounting portion 14 is not limited to the above. For example, the module mounting portion 14 may be formed on the rear surface of the seat frame 20 instead of the base frame 10.

The module passing portion 22 of the seat frame 20 may be formed on the front side of the module mounting portion 14 to allow the auxiliary massage module 100 to pass therethrough.

The auxiliary massage module 100 may be provided to be symmetrical with respect to the center of the massage apparatus 1. Hereinafter, a configuration of one side of the auxiliary massage module 100 will be described with reference to FIGS. 1 to 3.

Referring to FIG. 3, the auxiliary massage module 100 may include a first rotating member 1101.

The first rotating member 1101 may be connected to the module mounting portion 14 of the base frame 10. The first rotating member 1101 may be provided at the center thereof with a hole into which the module mounting portion 14 of the base frame 10 is inserted.

The first rotating member 1101 may be provided in a flange shape extending along a radial direction of the module mounting portion 14 of the base frame 10. However, the shape of the first rotating member 1101 is not limited thereto, and the first rotating member 1101 may be provided in various shapes as long as the rotation thereof is guided by the module mounting portion 14.

The auxiliary massage module 100 may include a first support member 120.

The first support member 120 may extend forward from the first rotating member 1101.

The first support member 120 may be positioned on the upper side of the user's shoulder.

The first support member 120 may include a first support bar 121 and a first shoulder massage case 122.

The first support bar 121 may connect the first rotating member 1101 to the first shoulder massage case 122. The first support bar 121 may be formed between the first rotating member 1101 and the first shoulder massage case 122. One end of the first support bar 121 may be connected to the first rotating member 1101, and the other end of the first support bar 121 may be connected to the first shoulder massage case 122.

The first support bar 121 may be formed to extend in a direction away from the seating surface 21 to be located on the upper side of the shoulder of the user seated on the seating surface 21.

The first shoulder massage case 122 may be connected to the first support bar 121.

The first shoulder massage case 122 may be provided inside thereof with a first accommodation space 1222. In other words, the inside of the first shoulder massage case 122 may be provided as an empty space.

A first shoulder massage ball 1221 may be disposed in the first accommodation space 1222 of the first shoulder massage case 122.

The first shoulder massage ball 1221 may be accommodated in the first shoulder massage case 122 and/or at least partially disposed in the first shoulder massage case 122 and protrude toward the seating surface 21. The first shoulder massage ball 1221 may be provided to protrude downward from the first shoulder massage case 122 and massage the user's shoulder.

Figure 7:
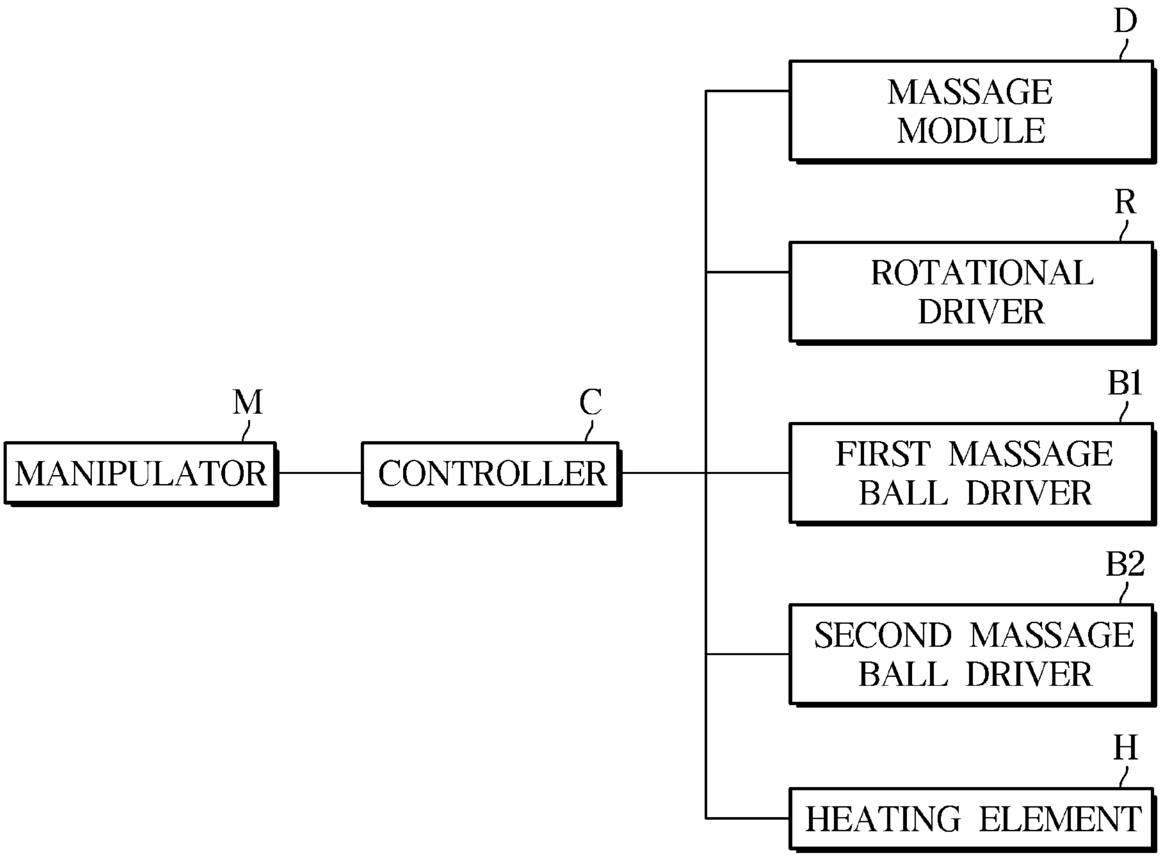
FIG. 7 is a schematic view illustrating a system for controlling a massage apparatus according to an embodiment of the present disclosure.

The first shoulder massage ball 1221 may include a plurality of acupressure protrusions and may be provided to rotate by a first massage ball driver (B1 in FIG. 7). However, the operation of the first shoulder massage ball 1221 is not limited thereto.

For example, the first shoulder massage ball 1221 may be provided to reciprocate in the upper-lower direction by the first massage ball driver B1. Alternatively, the first shoulder massage ball 1221 may be provided to reciprocate in the left-right direction or the front-back direction by the first massage ball driver B1.

The first shoulder massage ball 1221 may pass through the first shoulder massage case 122 and protrude outward of the first shoulder massage case 122.

However, the disclosure is not limited thereto, and a portion of the first shoulder massage case 122 that is in contact with the user's shoulder may include an elastically deformable material. Accordingly, the first shoulder massage ball 1221 may acupressure the user's shoulder on the inside of the first shoulder massage case 122 through the elastically deformable material of the first shoulder massage case 122.

The auxiliary massage module 100 may include a first extension member 140.

The first extension member 140 may be formed to extend downward from the first support member 120. The first support member 120 may be integrally formed with the first extension member 140.

The first extension member 140 may be located on a front side of the user's abdomen. The first extension member 140 may cover a front side of the user's upper body. The first extension member 140 may be connected to the first shoulder massage case 122.

The first extension member 140 may include a first connecting bar 141 and a first abdominal massage case 142.

The first connecting bar 141 may connect the first shoulder massage case 122 to the first abdominal massage case 142.

The first connecting bar 141 may include a first connection portion 1411 and a second connection portion 1412. The first connection portion 1411 of the first connecting bar 141 may be provided as a portion of the first connecting bar 141 connected to the first shoulder massage case 122.

The second connection portion 1412 of the first connecting bar 141 may be provided as a portion of the first connecting bar 141 connected to the first abdominal massage case 142.

The first connecting bar 141 may include a first bent portion 1413 and a first guard portion 1414.

The first bent portion 1413 may be formed to bend and extend downward from the first shoulder massage case 122. In other words, the first bent portion 1413 may be formed to bend and extend from the first connection portion 1411.

The first guard portion 1414 may connect the first bent portion 1413 to the first abdominal massage case 142. In other words, the first guard portion 1414 may connect the first bent portion 1413 to the second connection portion 1412.

The first guard portion 1414 may be located on the front side of a user seated on the seating surface 21. The first guard portion 1414 may be located on the front side of the user's body. The first guard portion 1414 may be provided to be disposed in a direction parallel to the seating surface 21 when the auxiliary massage module 100 operates.

The first abdominal massage case 142 may be provided inside thereof with a third accommodation space 1422. In other words, the inside of the first abdominal massage case 142 may be provided as an empty space.

A first abdominal massage ball 1421 may be at least partially disposed in the third accommodation space 1422 of the first abdominal massage case 142.

The first abdominal massage ball 1421 may be accommodated and/or at least partially disposed in the first abdominal massage case 142 and protrude from the first extension member 140 toward the seating surface 21.

However, the disclosure is not limited thereto, a portion of the first abdominal massage case 142 that is in contact with the user's abdomen may include an elastically deformable material. Accordingly, the first abdominal massage ball 1421 may acupressure the user's abdomen on the inside of the first abdominal massage case 142 through the elastically deformable material of the first abdominal massage case 142.

The first abdominal massage ball 1421 may include a plurality of acupressure protrusions and may be provided to rotate by a second massage ball driver (B2 in FIG. 7). However, the operation of the first abdominal massage ball 1421 is not limited thereto.

For example, the first abdominal massage ball 1421 may be provided to reciprocate in the upper-lower direction by the second massage ball driver B2. Alternatively, the first abdominal massage ball 1421 may be provided to reciprocate in the left-right direction or the front-back direction by the second massage ball driver B2.

A heating element H may be disposed in the third accommodation space 1422 of the first abdominal massage case 142. The heating element H may include a heater that dissipates heat.

Therefore, the massage apparatus 1 may perform a function of warming the user's abdomen through the heating element H mounted inside the first abdominal massage case 142.

The rotating member of the auxiliary massage module 100 may be provided in a pair.

The support member of the auxiliary massage module 100 may be provided in a pair.

The extension member of the auxiliary massage module 100 may be provided in a pair.

Hereinafter, the configuration of the other side opposite to one side of the auxiliary massage module 100 will be described with reference to FIGS. 1 to 3. The other side of the auxiliary massage module 100 may be symmetrically formed to include the same configuration as that of the one side of the auxiliary massage module 100 described above.

Referring to FIG. 3, the auxiliary massage module 100 may include a second rotating member 1102.

The second rotating member 1102 may be connected to the module mounting portion 14 of the base frame 10. The second rotating member 1102 may be provided at the center thereof with a hole into which the module mounting portion 14 of the base frame 10 is inserted.

The second rotating member 1102 may be provided in a flange shape extending along a radial direction of the module mounting portion 14 of the base frame 10. However, the shape of the second rotating member 1102 is not limited thereto, and the second rotating member 1102 may be provided in various shapes as long as the rotation thereof is guided by the module mounting portion 14.

The auxiliary massage module 100 may include a second support member 130.

The second support member 130 may extend forward from the second rotating member 1102.

The second support member 130 may be positioned on the upper side of the user's shoulder.

The second support member 130 may include a second support bar 131 and a second shoulder massage case 132.

The second support bar 131 may connect the second rotating member 1102 to the second shoulder massage case 132. The second support bar 131 may be formed between the second rotating member 1102 and the second shoulder massage case 132.

One end of the second support bar 131 may be connected to the second rotating member 1102, and the other end of the second support bar 131 may be connected to the second shoulder massage case 132.

The second support bar 131 may be formed to extend in a direction away from the seating surface 21 to be located on the upper side of the shoulder of the user seated on the seating surface 21.

The second shoulder massage case 132 may be connected to the second support bar 131.

The second shoulder massage case 132 may be provided inside thereof with a second accommodation space 1322. In other words, the inside of the second shoulder massage case 132 may be provided as an empty space.

A second shoulder massage ball 1321 may be disposed in the second accommodation space 1322 of the second shoulder massage case 132.

The second shoulder massage ball 1321 may be accommodated and/or at least partially disposed in the second shoulder massage case 132 and protrude toward the seating surface 21. The second shoulder massage ball 1321 may be provided to protrude downward from the second shoulder massage case 132 and massage the user's shoulder.

The second shoulder massage ball 1321 may include a plurality of acupressure protrusions and may be provided to rotate by a first massage ball driver (B1 in FIG. 7). However, the operation of the second shoulder massage ball 1321 is not limited thereto.

For example, the second shoulder massage ball 1321 may be provided to reciprocate in the upper-lower direction by the first massage ball driver B1. Alternatively, the second shoulder massage ball 1321 may be provided to reciprocate in the left-right direction or the front-back direction by the second massage ball driver B1.

The second shoulder massage ball 1321 may pass through the second shoulder massage case 132 and protrude outward of the second shoulder massage case 132.

However, the disclosure is not limited thereto, and a portion of the second shoulder massage case 132 that is in contact with the user's shoulder may include an elastically deformable material. Accordingly, the second shoulder massage ball 1321 may acupressure the user's shoulder on the inside of the second shoulder massage case 132 through the elastically deformable material of the second shoulder massage case 132.

The auxiliary massage module 100 may include a second extension member 150.

The second extension member 150 may be formed to extend downward from the second support member 130. The second support member 130 may be integrally formed with the second extension member 150.

The second extension member 150 may be located on a front side of the user's abdomen. The second extension member 150 may cover a front side of the user's upper body. The second extension member 150 may be connected to the second shoulder massage case 132.

The second extension member 150 may include a second connecting bar 151 and a second abdominal massage case 152.

The second connecting bar 151 may connect the second shoulder massage case 132 to the second abdominal massage case 152.

The second connecting bar 151 may include a third connection portion 1511 and a fourth connection portion 1512. The third connection portion 1511 of the second connecting bar 151 may be provided as a portion of the second connecting bar 151 connected to the second shoulder massage case 132.

The fourth connection portion 1512 of the second connecting bar 151 may be provided as a portion of the second connecting bar 151 connected to the second abdominal massage case 152.

The second connecting bar 151 may include a second bent portion 1513 and a second guard portion 1514.

The second bent portion 1513 may be formed to bend and extend downward from the second shoulder massage case 132. In other words, the second bent portion 1513 may be formed to bend and extend from the third connection portion 1511.

The second guard portion 1514 may connect the second bent portion 1513 to the second abdominal massage case 152. In other words, the second guard portion 1514 may connect the second bent portion 1513 to the fourth connection portion 1512.

The second guard portion 1514 may be located on the front side of a user seated on the seating surface 21. The second guard portion 1514 may be located on the front side of the user's body. The second guard portion 1514 may be provided to be disposed in a direction parallel to the seating surface 21 when the auxiliary massage module 100 operates.

The second abdominal massage case 152 may be provided inside thereof with a fourth accommodation space 1522. In other words, the inside of the second abdominal massage case 152 may be provided as an empty space.

A second abdominal massage ball 1521 may be disposed in the fourth accommodation space 1522 of the second abdominal massage case 152.

The second abdominal massage ball 1521 may be accommodated and/or at least partially disposed in the second abdominal massage case 152 and protrude from the second extension member 150 toward the seating surface 21.

However, the disclosure is not limited thereto, a portion of the second abdominal massage case 152 that is in contact with the user's abdomen may include an elastically deformable material. Accordingly, the second abdominal massage ball 1521 may acupressure the user's abdomen on the inside of the second abdominal massage case 152 through the elastically deformable material of the second abdominal massage case 152.

The second abdominal massage ball 1521 may include a plurality of acupressure protrusions and may be provided to rotate by a second massage ball driver (B2 in FIG. 7). However, the operation of the second abdominal massage ball 1521 is not limited thereto.

For example, the second abdominal massage ball 1521 may be provided to reciprocate in the upper-lower direction by the second massage ball driver B2. Alternatively, the second abdominal massage ball 1521 may be provided to reciprocate in the left-right direction or the front-back direction by the second massage ball driver B2.

A heating element H may be disposed in the fourth accommodation space 1522 of the second abdominal massage case 152. The heating element H may include a heater that dissipates heat.

Therefore, the massage apparatus 1 may perform a function of warming the user's abdomen through the heating element H mounted inside the second abdominal massage case 152.

Figure 4:
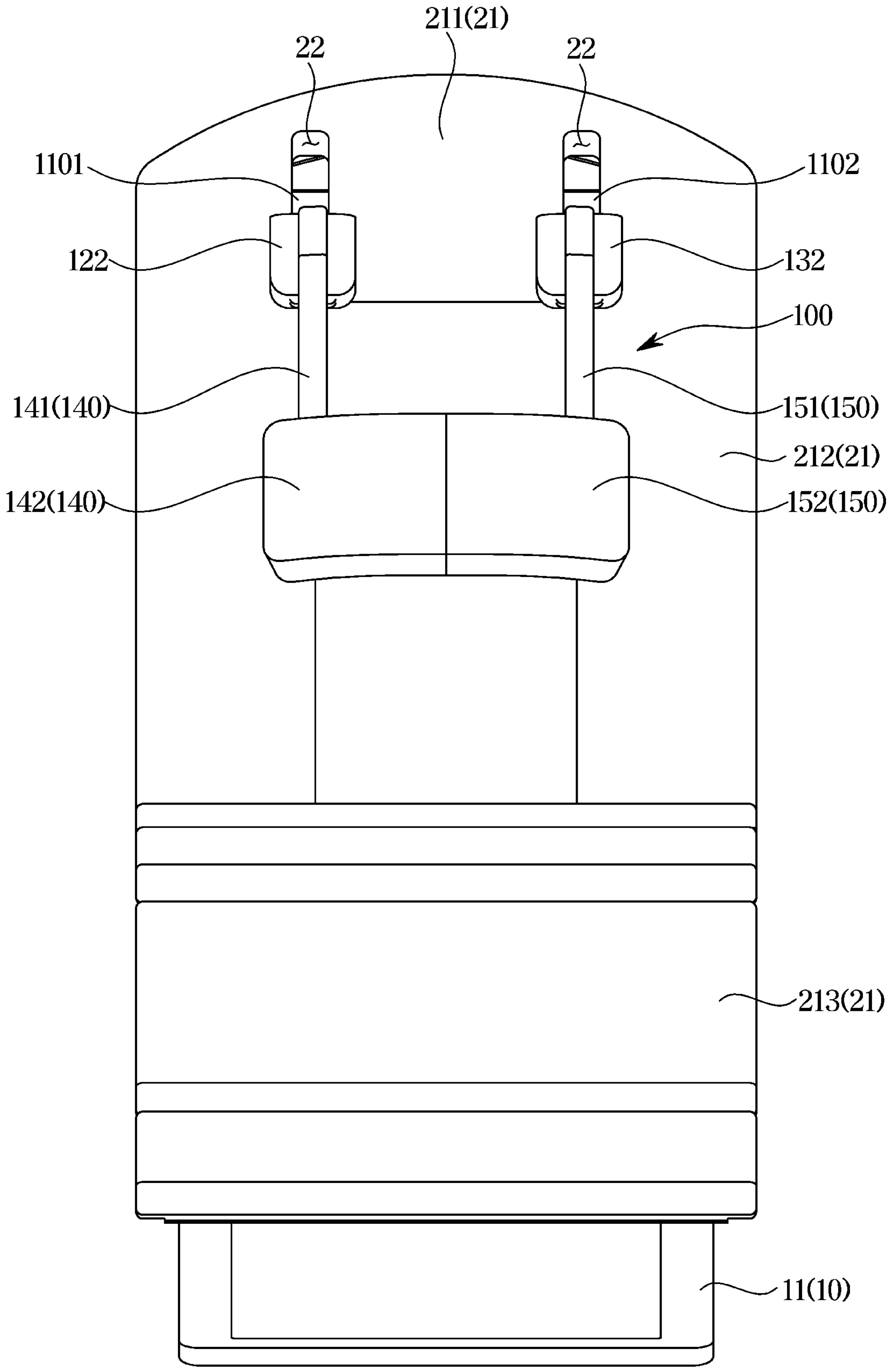
FIG. 4 is a front view illustrating the massage apparatus shown in FIG. 1.

FIG. 4 is a front view illustrating the massage apparatus 1 shown in FIG. 1.

Referring to FIG. 4, the auxiliary massage module 100 may pass through the seat frame through the module passing portion 22 of the seat frame. The module passing portion 22 may be formed by an opening in a portion of the seating surface 21 of the seat frame.

The rotation of the auxiliary massage module 100 may be supported by the first rotating member 1101 and the second rotating member 1102. The first rotating member 1101 and the second rotating member 1102 may be rotatably mounted on the module mounting portion 14 of the base frame 10 shown in FIG. 2.

The first rotating member 1101 and the second rotating member 1102 may be connected to the first shoulder massage case 122 and the second shoulder massage case 132, respectively.

The first shoulder massage case 122 may be connected to the first extension member 140. The second shoulder massage case 132 may be connected to the second extension member 150.

The first extension member 140 and the second extension member 150 may each be positioned on the front side of the seating surface 21. The first extension member 140 and the second extension member 150 may be provided in a bar shape elongated along the seating surface 21. The first extension member 140 and the second extension member 150 may form a pair of extension members that are symmetrical to each other.

The first abdominal massage case 142 and the second abdominal massage case 152 may be respectively connected to the pair of extension members to cover the abdomen of a user seated on the seating surface 21.

The first abdominal massage case 142 and the second abdominal massage case 152 may be integrally formed with each other. The first abdominal massage case 142 and the second abdominal massage case 152 may be located on the front side of the second seating portion 212 of the seating surface 21.

However, the shapes of the first abdominal massage case 142 and the second abdominal massage case 152 are not limited thereto, and the first abdominal massage case 142 and the second abdominal massage case 152 may be provided not to be connected to each other. Accordingly, the user may selectively care for the left side or right side abdomen of the body.

Figure 5:
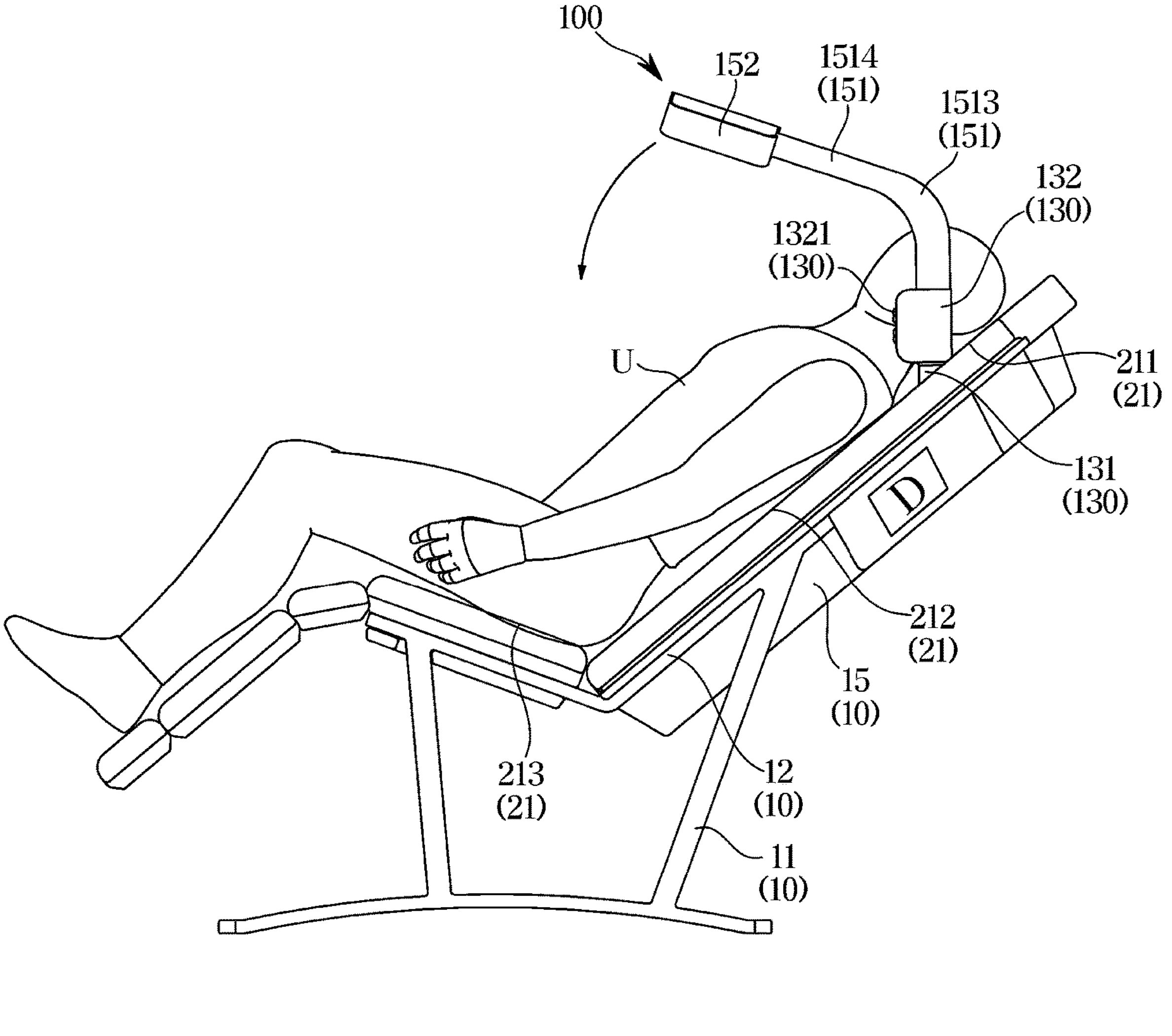
FIG. 5 is a side view illustrating a case in which an auxiliary massage module of the massage apparatus shown in FIG. 1 is in a first state.
Figure 6:
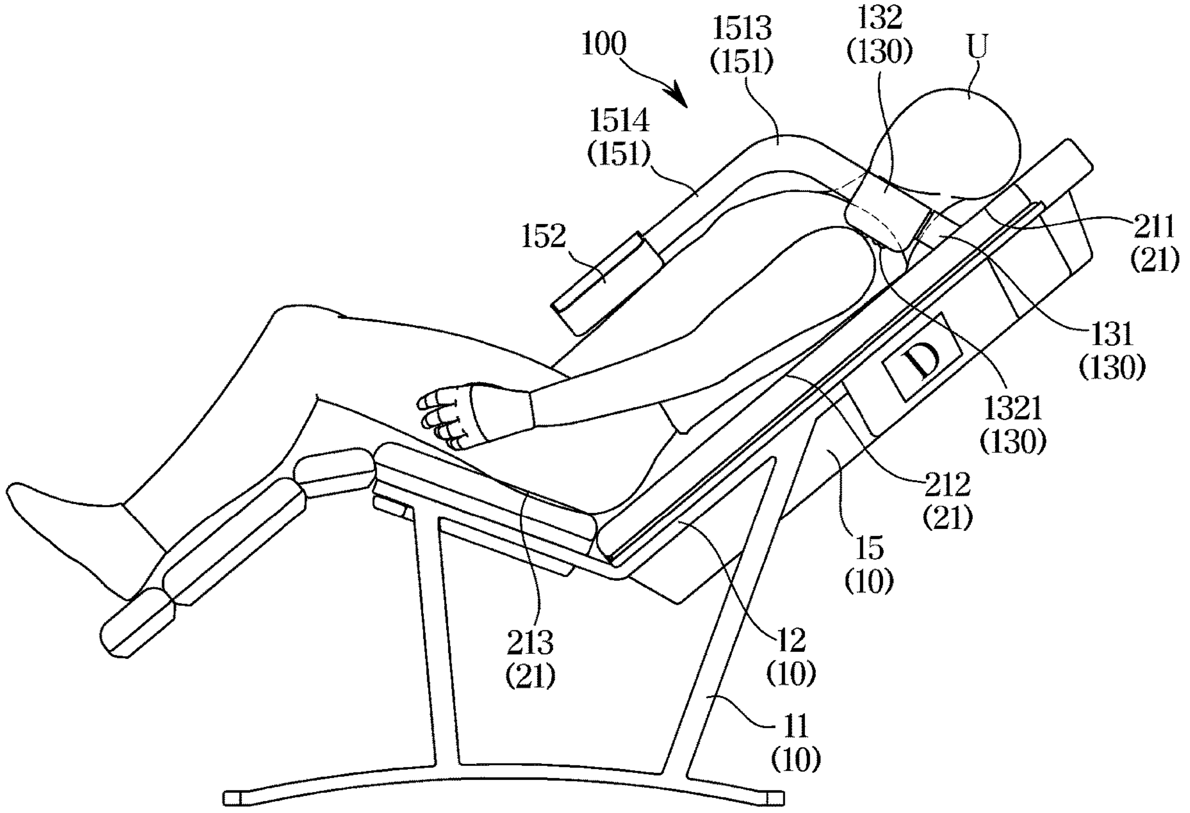
FIG. 6 is a side view illustrating a case in which an auxiliary massage module of the massage apparatus shown in FIG. 1 is in a second state.

FIG. 5 is a side view illustrating a case in which an auxiliary massage module of the massage apparatus shown in FIG. 1 is in a first state. FIG. 6 is a side view illustrating a case in which an auxiliary massage module of the massage apparatus shown in FIG. 1 is in a second state.

Referring to FIGS. 5 and 6, the massage apparatus 1 may include a massage module D.

The massage module D may be disposed between the base frame 10 and the seat frame 20. The massage module D may be provided to be movable along the seating surface 21 on the rear side of the seating surface 21 of the seat frame 20.

For example, the massage module D may be disposed between the seat frame 20 and the base frame 10 to press the rear surface of the user's body on the rear side of the seat frame 20 such that the massage module D is movable in the forward and backward directions and upward and downward directions with respect to the base frame 10 and the seat frame 20.

The massage module D may perform massage using a plurality of rollers on the rear side of the user. The number of massage modules is not limited thereto, and a module capable of providing massage to the user's lower body may be additionally provided separately from the module D disposed on the rear side of the second seating surface 21 to provide massage to the user's upper body.

The massage module D may convert a rotational motion of a motor into a reciprocating motion by a module driving device having an eccentric shaft to provide various massage modes, such as tapping, rubbing, and pressing, to the user. However, the operation method of the massage module D is not limited thereto.

Together with the operation of the massage module D performing the massage on the rear side of the user, the auxiliary massage module 100 may perform a massage on the front side of the user.

Alternatively, separately from the operation of the massage module D, the auxiliary massage module 100 may perform a massage on the front side of the user.

A case in which the auxiliary massage module 100 is in a first state will be described with reference to FIG. 5. Referring to FIG. 5, the auxiliary massage module 100 may be in a first state in which the auxiliary massage module 100 moves toward the user to provide a massage to the user's body.

In addition, FIG. 5 is a view shown from a user's left side, and operations of the second support member 130 and the second extension member 150 of the auxiliary massage module 100 will be described below. Since the first support member 120 and the first extension member 140 move together with the second support member 130 and the second extension member 150, descriptions of the first support member 120 and the first extension member 140 are omitted.

The first rotating member 1101 and the second rotating member 1102 of the auxiliary massage module 100 may be rotated by a rotational driver (R in FIG. 7).

As the second rotating member 1102 rotates, the second support bar 131 connected to the second rotating member 1102 may also move toward the user's shoulder. The second shoulder massage case 132 connected to the second support bar 131 may move to an area above the user's shoulder.

In addition, the second connecting bar 151 connected to the second shoulder massage case 132 and the second abdominal massage case 152 connected to the second connecting bar 151 may move toward the front side of the user's body.

Specifically, the second connecting bar 151 and the second abdominal massage case 152 may move in a direction closer to the user.

In addition, the second guard portion 1514 of the second connecting bar 151 may also move in a direction closer to the user.

A case in which the auxiliary massage module 100 is in a second state will be described with reference to FIG. 6. Referring to FIG. 6, the auxiliary massage module 100 may be in a second state in which the auxiliary massage module 100 presses the user's body to provide a massage to the user's body.

In the second state, the second shoulder massage case 132 of the auxiliary massage module 100 may be disposed on the upper side of the user's shoulder. In this case, the second shoulder massage ball 1321 accommodated in the second shoulder massage case 132 may be in contact with the user's shoulder. The second shoulder massage ball 1321 may press the upper side of the user's shoulder to acupressure the user's shoulder.

The second bent portion 1513 may be formed to extend from the second shoulder massage case 132 and form a space in which the user may be accommodated on the rear side of the auxiliary massage module 100. The second guard portion 1514 extending downward from the second bent portion 1513 may cover the front side of the user's upper body.

The second abdominal massage case 152 connected to the second guard portion 1514 may come into contact with the user's abdomen.

Specifically, the second abdominal massage case 152 may be provided to warm the user's abdomen using heat emitted from the heating element H when performing an abdominal heating mode.

In addition, the second abdominal massage case 152 may be provided to massage the user's abdomen using the second abdominal massage ball 1521 when performing an abdominal massage mode.

Although not shown in the drawing, the first shoulder massage case 122 and the second shoulder massage case 132 may be provided to emit fragrance to the user.

In addition, the first shoulder massage case 122 and the second shoulder massage case 132 may be provided to transmit sound to the user. That is, the first shoulder massage case 122 and the second shoulder massage case 132 may be provided to serve as a type of speaker.

FIG. 7 is a schematic view illustrating a system for controlling a massage apparatus according to an embodiment of the present disclosure.

Referring to FIG. 7, a user's command may be input to the massage apparatus 1 through the manipulator M. The user may select various massage modes through the manipulator M provided as a touch panel or the like.

However, it is not limited thereto, and the user may use a smartphone as a manipulator M to transmit a signal related to a massage mode to the controller C.

The controller C may receive a signal related to performing a massage mode from the manipulator M.

Specifically, the controller C may control the operations of the massage module D, the first massage ball driver B1 and the second massage ball driver B1 of the auxiliary massage module 100.

The controller C may control the vertical movement of the massage module D. As the controller C may control the vertical movement of the massage module D, the massage apparatus 1 may massage the user's body in the vertical direction.

The controller C may perform a massage mode of the massage module D. Specifically, the massage module D may perform various massage modes, such as a tapping mode, a rubbing mode, a pressing mode, and the like. Accordingly, the controller C may control driving of the massage module to provide various massage modes to the user.

The controller C may control the rotational driver R, the first massage ball driver B1, and the second massage ball driver B2 of the auxiliary massage module 100.

The rotational driver R may provide rotational power of the auxiliary massage module 100. Specifically, the rotational driver R may provide power for rotating the module mounting portion 14 of the base frame 10 to which the first rotating member 1101 and the second rotating member 1102 of the auxiliary massage module 100 are coupled.

The rotational driver R may be located between the base frame 10 and the seat frame 20. However, the location of the rotational driver R is not limited thereto and the rotational driver R may be disposed on the outside of the base frame 10 to transmit power to the module mounting portion 14.

The controller C may control the rotational driver R to control rotation of the auxiliary massage module 100. Specifically, the controller C may, upon receiving a user's command, control the rotational driver R such that the auxiliary massage module 100 rotates toward the user.

In addition, the controller C may control the rotational driver R for the auxiliary massage module 100 to move toward the seating surface 21 such that the user is kept seated on the seating surface 21.

Therefore, the configuration of the auxiliary massage module 100 may allow the user to be in close contact with the seating surface 21 of the seat frame 20. As a result, the massage efficiency of the massage apparatus 1 may be increased.

The first massage ball drivers B1 may drive the first shoulder massage ball 1221 and the second shoulder massage ball 1321. The first massage ball drivers B1 may provide power for driving the first shoulder massage ball 1221 and the second shoulder massage ball 1321.

The controller C may, upon receiving a user's command, control the first massage ball driver B1 to perform a shoulder massage mode.

The first massage ball drivers B1 may be accommodated inside the first shoulder massage case 122 and the second shoulder massage case 132 together with the first shoulder massage ball 1221 and the second shoulder massage ball 1321.

Alternatively, the first massage ball drivers B1 may be disposed between the base frame 10 and the seat frame 20, and provided to transmit power to the first shoulder massage ball 1221 and the second shoulder massage ball 1321 through a support member and an extension member corresponding thereto.

The second massage ball drivers B2 may drive the first abdominal massage ball 1421 and the second abdominal massage ball 1521.

The second massage ball drivers B2 may provide power to drive the first abdominal massage ball 1421 and the second abdominal massage ball 1521.

The controller C may, upon receiving a user's command, control the second massage ball driver B2 to perform an abdominal massage mode.

The second massage ball drivers B2 may be accommodated inside the first abdominal massage case 142 and the second abdominal massage case 152 together with the first abdominal massage ball 1421 and the second abdominal massage ball 1521. Alternatively, the second massage ball drivers B2 may be disposed between the base frame 10 and the seat frame 20, and provide power to the first abdominal massage ball 1421 and the second abdominal massage ball 1521 through a support member and extension member corresponding thereto.

The controller C may control the heating element H. More specifically, the controller C may control the heating temperature of the heating element H. Accordingly, the controller C may, upon receiving a user's command, control the temperature of the heating element H to perform an abdominal heating mode in which the user's abdomen is warmed.

The massage apparatus 1 according to an embodiment of the disclosure includes an auxiliary massage module coupled to the front side of the massage apparatus 1, and thus a massage on the front surface of the user's body can be performed with a simple operation.

In addition, close contact between the user and the massage apparatus 1 is assisted through the auxiliary massage module, and thus the massage efficiency of the massage apparatus 1 can be increased.

In addition, care for the user's abdomen, such as heating or massage, can be performed using an auxiliary massage module.

Although the disclosure has been shown and described in relation to specific embodiments, it would be appreciated by those skilled in the art that changes and modifications may be made in these embodiments without departing from the principles and scope of the disclosure, the scope of which is defined in the claims and their equivalents.

The invention claimed is:

1. A massage apparatus comprising:

a base frame;

a seat frame coupled to the base frame to form a seating surface on one side;

a massage module disposed between the base frame and the seat frame and provided to be movable along the seating surface on a rear side of the seating surface; and an auxiliary massage module formed to pass through the seat frame, wherein the auxiliary massage module includes:

a rotating member connected to a module mounting portion of the base frame that forms a rotation axis of the auxiliary massage module;

a support member formed to extend forward from the rotating member and having a shoulder massage case;

an extension member formed to extend downward from the support member and having an abdominal massage case; and wherein the seat frame includes a module passing portion formed as an opening in a portion of the seating surface to be positioned on a front of the module mounting portion so that the auxiliary massage module passes therethrough.

2. The massage apparatus of claim 1, further comprising a shoulder massage ball disposed in the shoulder massage cases and protruding toward the seating surface.

3. The massage apparatus of claim 1, further comprising a heating element disposed in the abdominal massage case.

4. The massage apparatus of claim 3, further comprising an abdominal massage ball disposed in the abdominal massage case and protruding from the extension member toward the seating surface.

5. The massage apparatus of claim 3, wherein the apparatus comprises a pair of the extension member, a pair of the abdominal massage case, and each of the pair of abdominal massage cases is connected to a corresponding one of the pair of extension members and configured to cover an abdomen of a user seated on the seating surface.

6. The massage apparatus of claim 5, wherein each of the pair of abdominal massage cases is provided therein with an accommodation space, and the heating element is accommodated in the accommodation space.

7. The massage apparatus of claim 1, wherein the support member is integrally formed with the extension member.

8. The massage apparatus of claim 1, wherein the support member includes a support bar connecting the rotating member to the shoulder massage case.

9. The massage apparatus of claim 8, wherein the support bar extends in a direction away from the seating surface and configured to be located on an upper side of a shoulder of a user seated on the seating surface.

10. The massage apparatus of claim 1, wherein the extension member includes a connecting bar that includes a bent portion connecting the shoulder massage case to the abdominal massage case and formed to bend and extend downward from the shoulder massage case.

11. The massage apparatus of claim 10, wherein the connecting bar includes a guard portion connecting the bent portion to the abdominal massage case and configured to be positioned on a front of a user on the seating surface.

12. The massage apparatus of claim 1, further comprising:

a controller configured to control operations of the massage module and the auxiliary massage module; and a rotational driver configured to provide rotational power for rotating the auxiliary massage module, wherein the controller controls the rotational driver to move the auxiliary massage module toward the seating surface so that a user is kept seated on the seating surface.

13. The massage apparatus of claim 12, further comprising:

an abdominal massage ball disposed inside the abdominal massage case; and a massage ball driver configured to drive the abdominal massage ball, wherein the controller controls the massage ball driver to perform an abdominal massage mode.

14. The massage apparatus of claim 12, further comprising a heating element accommodated inside the abdominal massage cases;

the controller controls a heating temperature of the heating element to perform an abdominal heating mode.

15. The massage apparatus of claim 12, further comprising:

a manipulator disposed on a housing of the massage apparatus, wherein the manipulator is configured to receive a command input from the user and to responsively provide control signals to the controller.

16. The massage apparatus of claim 1, wherein a portion of the shoulder massage case includes an elastically deformable material, and wherein a shoulder massage ball is configured to acupressure a shoulder of a user from inside of the shoulder massage case using the elastically deformable material.

* * * * *